(12) United States Patent
Hanlon et al.

(10) Patent No.: US 9,228,934 B2
(45) Date of Patent: *Jan. 5, 2016

(54) FLOW CELL MODULES AND LIQUID SAMPLE ANALYZERS AND METHODS INCLUDING SAME

(71) Applicant: PerkinElmer Health Sciences, Inc., Waltham, MA (US)

(72) Inventors: Gregory Hanlon, Windsor, CT (US); Timothy Neal, Harwinton, CT (US); Richard Edwards, Brookfield, CT (US)

(73) Assignee: PerkinsElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,066

(22) Filed: Jun. 17, 2015

(65) Prior Publication Data

US 2015/0285732 A1    Oct. 8, 2015

Related U.S. Application Data

(63) Continuation of application No. 14/276,509, filed on May 13, 2014, now Pat. No. 9,091,629, which is a continuation of application No. 13/781,025, filed on Feb. 28, 2013, now Pat. No. 8,760,658.

(60) Provisional application No. 61/762,588, filed on Feb. 8, 2013, provisional application No. 61/713,401, filed on Oct. 12, 2012.

(51) Int. Cl.
*G01N 21/05* (2006.01)
*G01N 21/59* (2006.01)

(52) U.S. Cl.
CPC ............... *G01N 21/05* (2013.01); *G01N 21/59* (2013.01); *G01N 2021/052* (2013.01)

(58) Field of Classification Search
USPC ............ 356/440, 246, 240, 436, 432; 385/12, 385/14, 125, 132, 141
See application file for complete search history.

(56) References Cited

U.S. PATENT DOCUMENTS 5,153,679 A    10/1992    Gilby
(Continued)

FOREIGN PATENT DOCUMENTS

EP    0089 157 A1    9/1983
EP    2 124 036 A1    11/2009

OTHER PUBLICATIONS

Stoma® Flow Cells for Spectophotometers, Retrieved Aug. 3, 2012 from URL http://www.starna.com/ukhome/d cells/d_cells_s/flow/xflow.html , 3 pages.
(Continued)

*Primary Examiner* — Sang Nguyen
(74) *Attorney, Agent, or Firm* — Myers Bigel Sibley & Sajovec, PA

(57) ABSTRACT

A flow cell module for use in a liquid sample analyzer includes a module housing, a liquid core waveguide mounted in the module housing to receive a flow of a liquid sample from a liquid sample source, an input optical fiber disposed in the module housing to transmit radiation from a radiation source to the liquid core waveguide, an input termination located on an input end of the input optical fiber, a first kinematic connection mechanism operative to bias the input termination in a first direction along a first axis while permitting displacement of the input termination in a first opposing direction along the first axis, and a second kinematic connection mechanism operative to bias the input termination in a second direction along a second axis while permitting displacement of the input termination in a second opposing direction along the second axis. The second axis is transverse to the first axis.

20 Claims, 14 Drawing Sheets

(56) References Cited

U.S. PATENT DOCUMENTS

| | | | |
|---|---|---|---|
| 5,184,192 A | 2/1993 | Gilby et al. | |
| 5,416,879 A | 5/1995 | Liu | |
| 5,444,807 A | 8/1995 | Liu | |
| 5,608,517 A | 3/1997 | Munk | |
| 5,877,409 A | 3/1999 | Girling | |
| 6,020,207 A * | 2/2000 | Liu | 436/164 |
| 6,188,813 B1 | 2/2001 | Dourdeville et al. | |
| 6,314,227 B1 | 11/2001 | Nath | |
| 6,526,188 B2 | 2/2003 | Dourdeville et al. | |
| 6,542,231 B1 | 4/2003 | Garrett | |
| 6,678,051 B2 | 1/2004 | Gerner et al. | |
| 6,734,961 B2 | 5/2004 | Gerner et al. | |
| 6,878,943 B2 * | 4/2005 | Tao et al. | 250/373 |
| 7,005,090 B2 | 2/2006 | Mueller et al. | |
| 7,259,840 B1 | 8/2007 | Gerner et al. | |
| 7,298,472 B2 | 11/2007 | Gerner et al. | |
| 7,362,429 B2 | 4/2008 | Gilby | |
| 7,515,259 B2 | 4/2009 | Hilmer et al. | |
| 7,574,076 B2 | 8/2009 | Mueth et al. | |
| 7,593,101 B2 | 9/2009 | Yakimoski et al. | |
| 7,716,995 B2 | 5/2010 | Patten et al. | |
| 7,808,619 B2 | 10/2010 | Gerner et al. | |
| 7,847,944 B2 | 12/2010 | Buettner et al. | |
| 7,859,657 B2 | 12/2010 | Jeannotte et al. | |
| 7,914,852 B2 | 3/2011 | Belz et al. | |
| 8,206,987 B2 | 6/2012 | Durack et al. | |
| 8,401,346 B2 | 3/2013 | Jeannotte et al. | 385/12 |
| 9,086,533 B1 * | 7/2015 | Wach | |
| 2002/0041726 A1 * | 4/2002 | Thackara | 385/16 |
| 2002/0071123 A1 | 6/2002 | Miller et al. | |
| 2005/0140971 A1 | 6/2005 | Yamaguchi et al. | |
| 2006/0257089 A1 * | 11/2006 | Mueth et al. | 385/125 |
| 2009/0009758 A1 | 1/2009 | Gilby | |
| 2009/0230028 A1 * | 9/2009 | Mueller et al. | 209/209 |
| 2011/0141465 A1 | 6/2011 | Jeannotte et al. | |
| 2011/0149286 A1 | 6/2011 | Wu et al. | |

OTHER PUBLICATIONS

International Search Report and Written Opinion issued in corresponding PCT Application No. PCT/US2013/063922, mailed Jan. 22, 2014 (11 pages).

* cited by examiner

FLOW CELL MODULES AND LIQUID SAMPLE ANALYZERS AND METHODS INCLUDING SAME

RELATED APPLICATION(S)

The present application is a continuation application (indirect divisional application) of and claims priority from U.S. patent application Ser. No. 14/276,509, filed May 13, 2014, which is a continuation application of and claims priority from U.S. patent application Ser. No. 13/781,025, filed Feb. 28, 2013, issued as U.S. Pat. No. 8,760,658, which claims the benefit of and priority from U.S. Provisional Patent Application No. 61/762,588, filed Feb. 8, 2013, and U.S. Provisional Patent Application Ser. No. 61/713,401, filed Oct. 12, 2012, the disclosures of which are incorporated herein by reference in their entireties.

FIELD

The present technology relates to liquid sample analyzers and flow cell modules therefor.

BACKGROUND

Liquid sample analyzers of known design include a flow cell, a light source for providing light to the flow cell, a liquid sample source for flowing a liquid sample through the flow cell, and a detector (e.g., a spectrometer) for receiving light from the flow cell (i.e., the light from the light source as modified by transmission through the flow of the liquid sample in the flow cell). It may be necessary or desirable to remove a given flow cell from the system (i.e., from between the light source and the detector) and reinstall the flow cell or replace it with a new flow cell. For this purpose, it is known to package a flow cell in a flow cell module that can be inserted between and removed from the system.

SUMMARY

According to embodiments of the present technology, a flow cell module for use in a liquid sample analyzer, the liquid sample analyzer including a radiation source, a sensing device, and a liquid sample source, includes a module housing, a liquid core waveguide, an input optical fiber, an input termination, and first and second kinematic connection mechanisms. The liquid core waveguide is mounted in the module housing and is configured to receive a flow of a liquid sample from the liquid sample source. The input optical fiber is disposed in the module housing and is configured to transmit radiation from the radiation source to the liquid core waveguide. The input termination is located on an input end of the input optical fiber. The first kinematic connection mechanism is operative to bias the input termination in a first direction along a first axis while permitting displacement of the input termination in a first opposing direction along the first axis. The second kinematic connection mechanism is operative to bias the input termination in a second direction along a second axis while permitting displacement of the input termination in a second opposing direction along the second axis. The second axis is transverse to the first axis.

In some embodiments, the first and second axes are substantially perpendicular.

According to some embodiments, the first kinematic connection mechanism includes a first spring biasing the input termination in the first direction, and the second kinematic connection mechanism includes a second spring biasing the input termination in the second direction. In some embodiments, the first spring is a coil spring and the second spring is a leaf spring.

In some embodiments, the input optical fiber is flexible.

The flow cell module may further include: an output optical fiber disposed in the module housing and configured to transmit radiation from the liquid core waveguide to the sensing device; and an output termination on an output end of the output optical fiber, wherein the output termination is kinematically mounted in the module housing. The flow cell module may include a third kinematic connection mechanism operative to bias the output termination in a third direction along a third axis while permitting displacement of the output termination in a third opposing direction along the third axis. In some embodiments, the third kinematic connection mechanism includes a third spring biasing the output termination in the third direction.

According to some embodiments of the present technology, a flow cell module for use in a liquid sample analyzer, the liquid sample analyzer including a radiation source, a sensing device and a liquid sample source, includes a module housing, a liquid core waveguide, an output optical fiber, and an output termination. The liquid core waveguide is mounted in the module housing and is configured to receive a flow of a liquid sample from the liquid sample source. The output optical fiber is disposed in the module housing and is configured to transmit radiation from the liquid core waveguide to the sensing device. The output termination is located on an output end of the output optical fiber. The output termination is kinematically mounted in the module housing.

The flow cell module may include a kinematic connection mechanism operative to bias the output termination in a prescribed direction along a displacement axis while permitting displacement of the output termination in an opposing direction along the displacement axis. In some embodiments, the kinematic connection mechanism includes a spring biasing the output termination in the prescribed direction. According to some embodiments, the output optical fiber is flexible.

According to embodiments of the present technology, a flow cell module for use in a liquid sample analyzer, the liquid sample analyzer including a radiation source, a sensing device and a liquid sample source, includes a module housing, a liquid core waveguide, a flexible input optical fiber, an input termination, a flexible output optical fiber, and an output termination. The liquid core waveguide is mounted in the module housing and is configured to receive a flow of a liquid sample from the liquid sample source. The input optical fiber is disposed in the module housing and is configured to transmit radiation from the radiation source to the liquid core waveguide. The input termination is located on an input end of the input optical fiber. The flexible output optical fiber is disposed in the module housing and is configured to transmit radiation from the liquid core waveguide to the sensing device. The output termination is located on an output end of the output optical fiber.

In some embodiments, the input termination and the output termination are each mounted in the module housing.

According to some embodiments of the present technology, a liquid sample analyzer has a holding slot and includes a radiation source, a sensing device, a liquid sample source, an alignment structure associated with the radiation source, and a flow cell module configured to be mounted in the holding slot. The flow cell module includes: a module housing; a liquid core waveguide mounted in the module housing and configured to receive a flow of a liquid sample from the liquid sample source; an input optical fiber disposed in the module housing and configured to transmit radiation from the radiation source to the liquid core waveguide; an input termination on an input end of the input optical fiber; a first kinematic connection mechanism operative to bias the input termination in a first direction along a first axis while permitting displacement of the input termination in a first opposing direction along the first axis; and a second kinematic connection mechanism operative to bias the input termination in a second direction along a second axis while permitting displacement of the input termination in a second opposing direction along the second axis. The second axis is transverse to the first axis. The first kinematic connection mechanism and the second kinematic connection mechanism cooperate to automatically align the input termination with the alignment structure when the flow cell module is inserted into the holding slot to thereby properly position the input termination with respect to the radiation source.

In some embodiments, the alignment structure includes an alignment block adjacent the radiation source. The alignment block has a sidewardly open groove defined therein and configured to receive the input termination. The groove has a lengthwise groove axis. When the flow cell module is inserted into the holding slot, the first axis extends substantially parallel with the lengthwise groove axis and the first kinematic connection mechanism tends to bias the input termination towards the radiation source, and the second direction intersects the groove so that the second kinematic connection mechanism tends to bias the input termination toward a base of the groove.

According to some embodiments, the flow cell module further includes an output optical fiber and an output termination. The output optical fiber is disposed in the module housing and is configured to transmit radiation from the liquid core waveguide to the sensing device. The output termination is located on an output end of the output optical fiber. The output termination is kinematically mounted in the module housing to facilitate alignment between the output termination and the sensing device when the flow cell module is inserted into the holding slot.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

Figure 1:
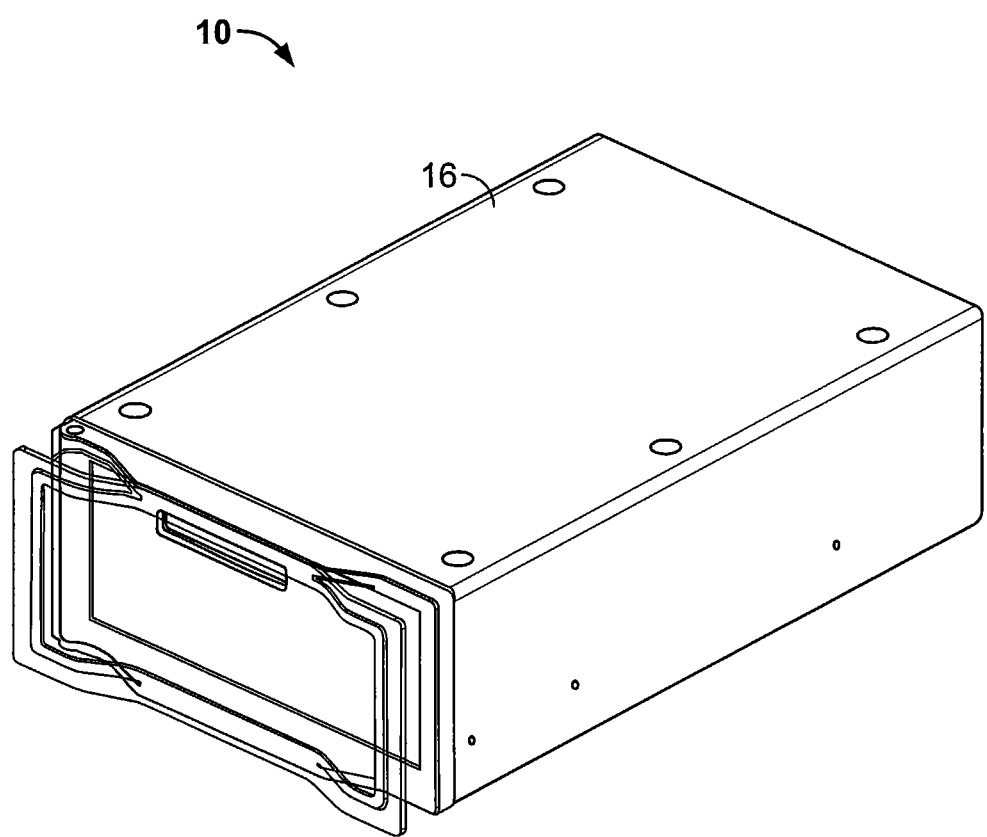
FIG. 1 is a front perspective view of a liquid sample analyzer including a flow cell module according to embodiments of the technology.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

As used herein, "kinematically mounted" means the subject component is mounted on or coupled to another component so as to provide or permit relative movement between the two components.

Embodiments of the present technology are directed to flow cell modules and liquid sample analyzers incorporating the same. Flow cell modules as disclosed herein can be used in photometric apparatus for spectroscopic analysis, such as high performance chromatography (HPLC), capillary LC, and capillary electrophoresis (CE). In general, the flow cell module includes a flow cell assembly mounted or packaged in a module housing or casing to facilitate ease of use and handling. The flow cell assembly provides a flow through liquid waveguide having a waveguide bore through which a stream of a liquid sample is flowed. The flow cell assembly provides fluidics for introducing the liquid sample into and removing the liquid sample from the waveguide bore. The flow cell assembly also provides a source optical fiber to guide radiation (e.g., UV or visible light) from a radiation source to the waveguide and a detector optical fiber to guide the radiation from the waveguide to a sensing device. The light from the light source optical fiber is guided from the source optical fiber to the detector optical fiber through the waveguide and the liquid sample flowing therethrough by total internal reflection at the boundary between the liquid sample and the waveguide bore, for example. Ends of the optical fiber and the detector optical fiber are kinematically mounted in the housing of the flow cell module to enable convenient and effective connections between the fiber ends, the light source and the detector.

Figure 3:
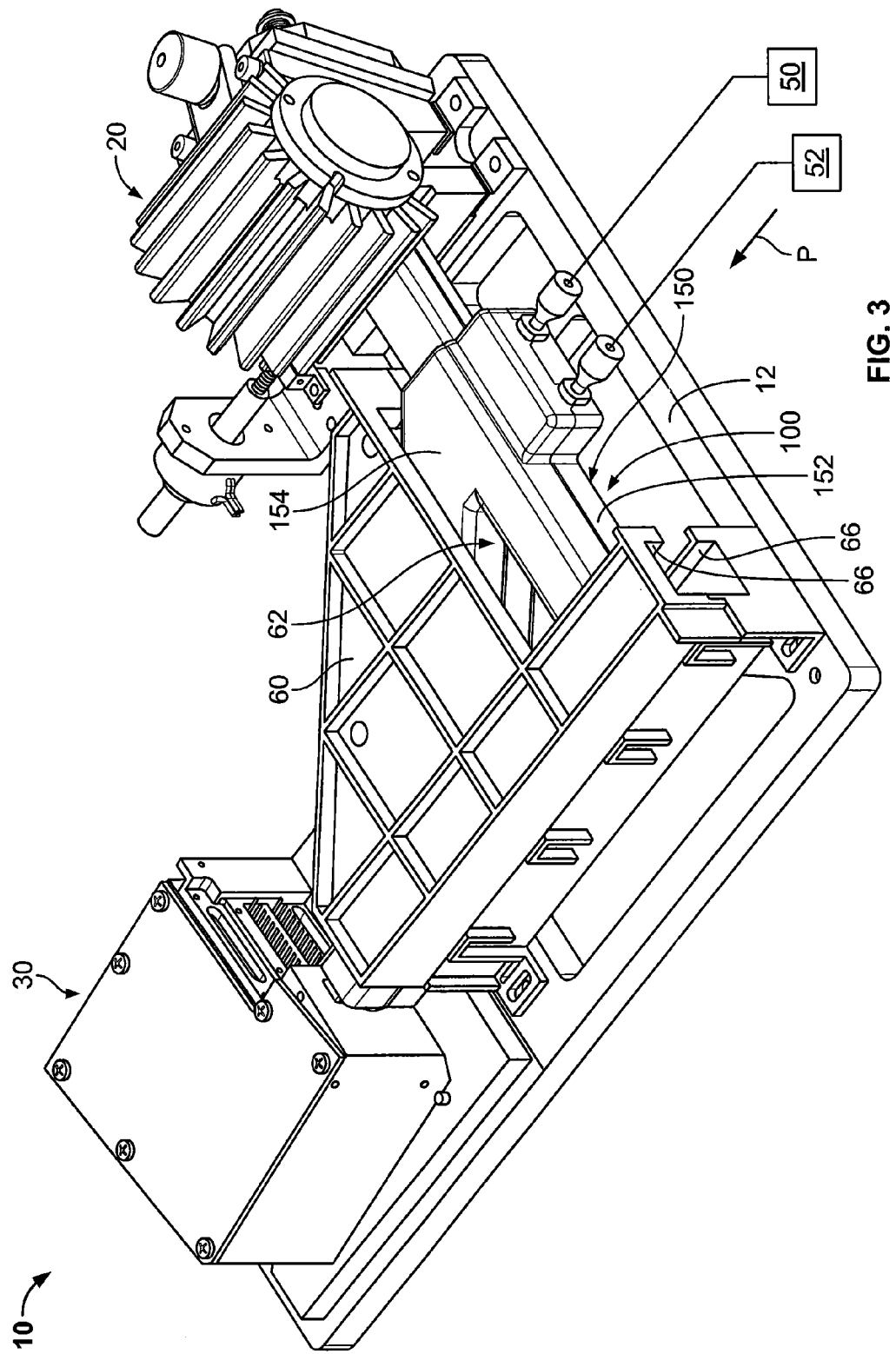
FIG. 3 is a perspective view of a subassembly forming a part of the liquid sample analyzer of FIG. 1.

With reference to the figures, a liquid sample analyzer 10 including a flow cell module 100 according to embodiments of the technology is shown therein. The liquid sample analyzer 10 further includes a remote radiation or light source 20, a remote sensing device or detector 30, and a carrier tray 60 affixed to a shared base 12, and also a remote liquid sample source 50 (FIG. 3) and a remote liquid sample receiver 52. Some or all of these components may be housed in a cabinet 16 (FIG. 1), for example.

Figure 6:
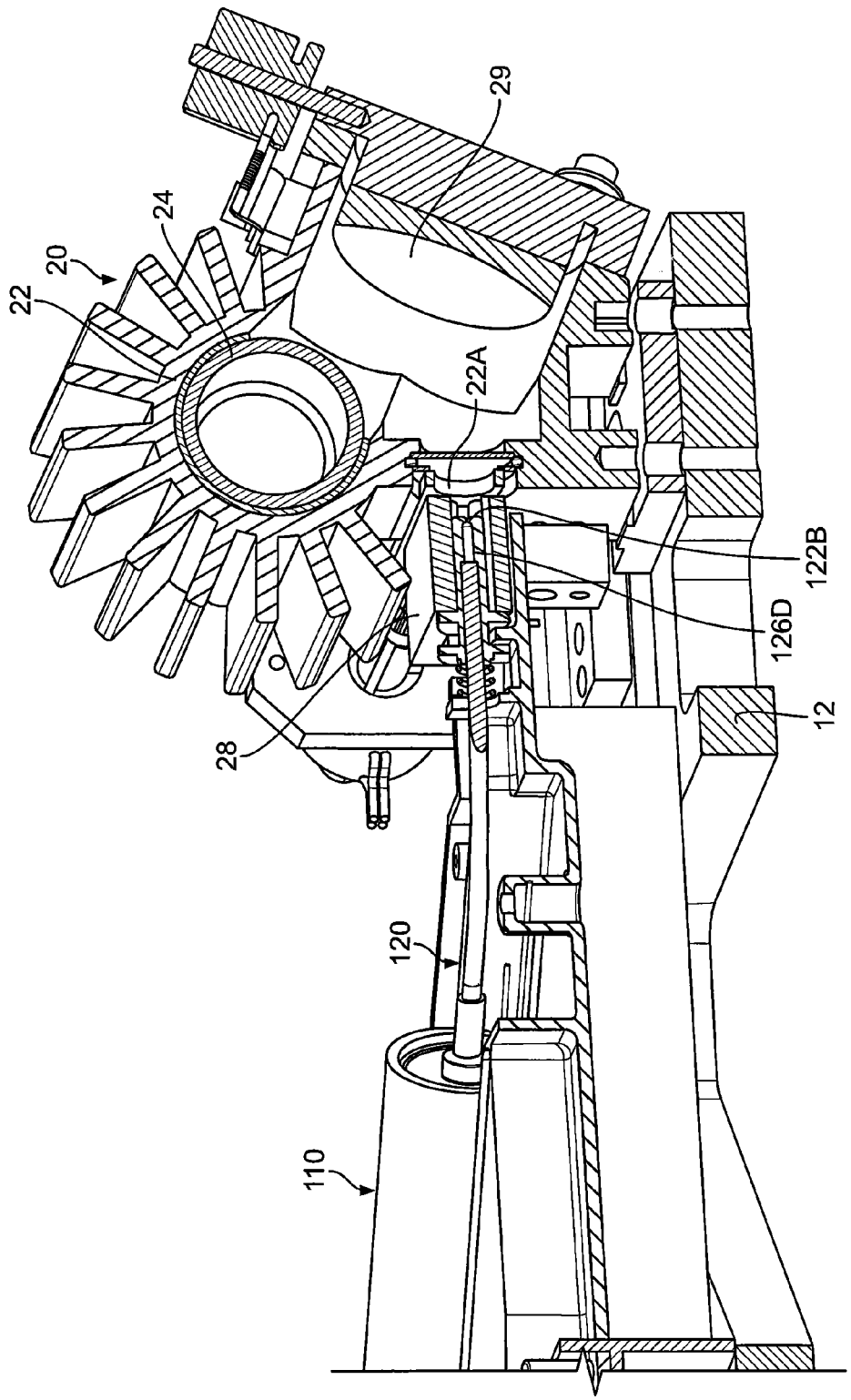
FIG. 6 is a further fragmentary, perspective view of the subassembly of FIG. 3.
Figure 7:
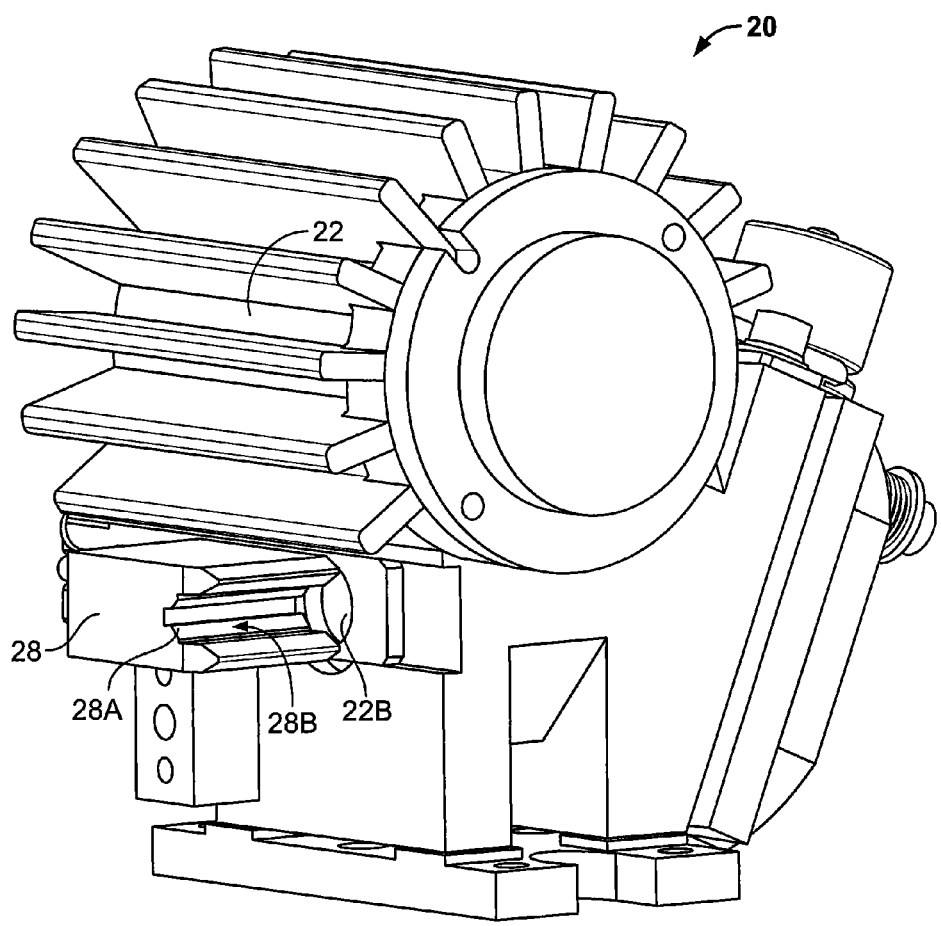
FIG. 7 is a perspective view of a light source forming a part of the liquid sample analyzer of FIG. 1.
Figure 8:
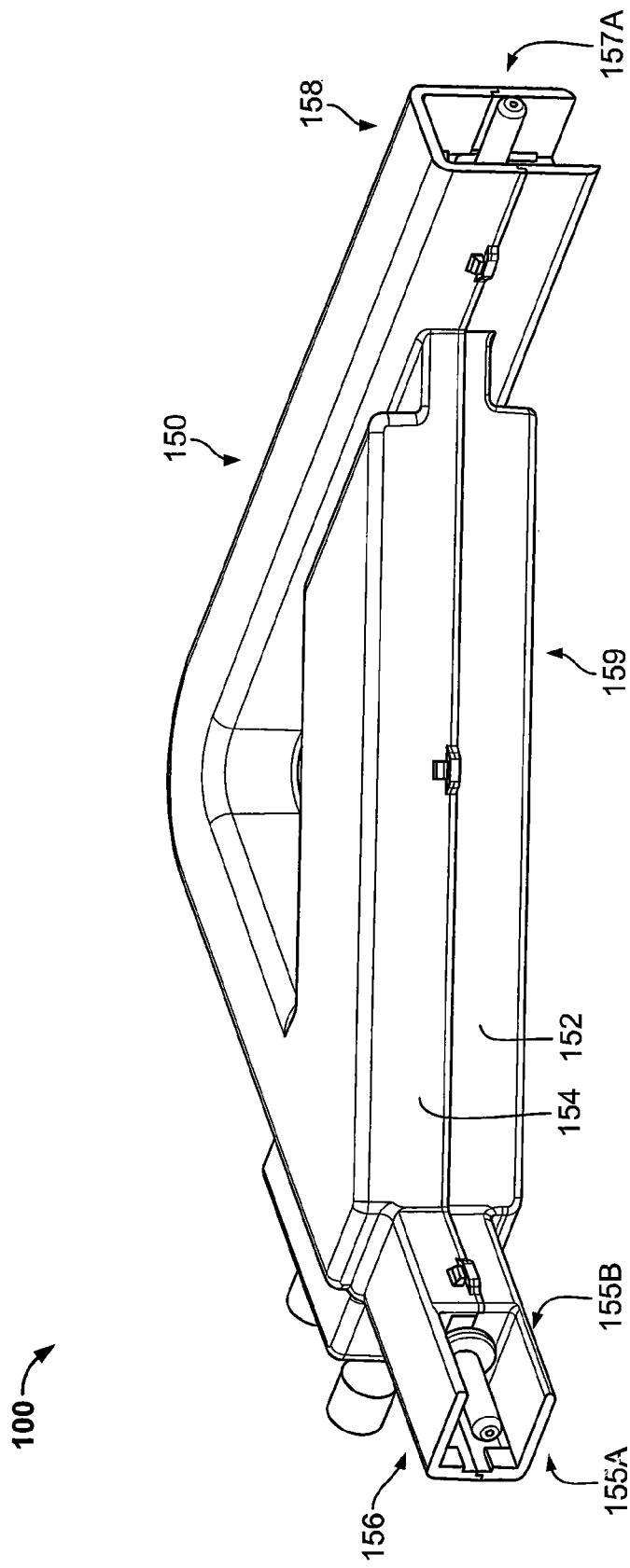
FIG. 8 is a rear perspective view of the flow cell module.
Figure 9:
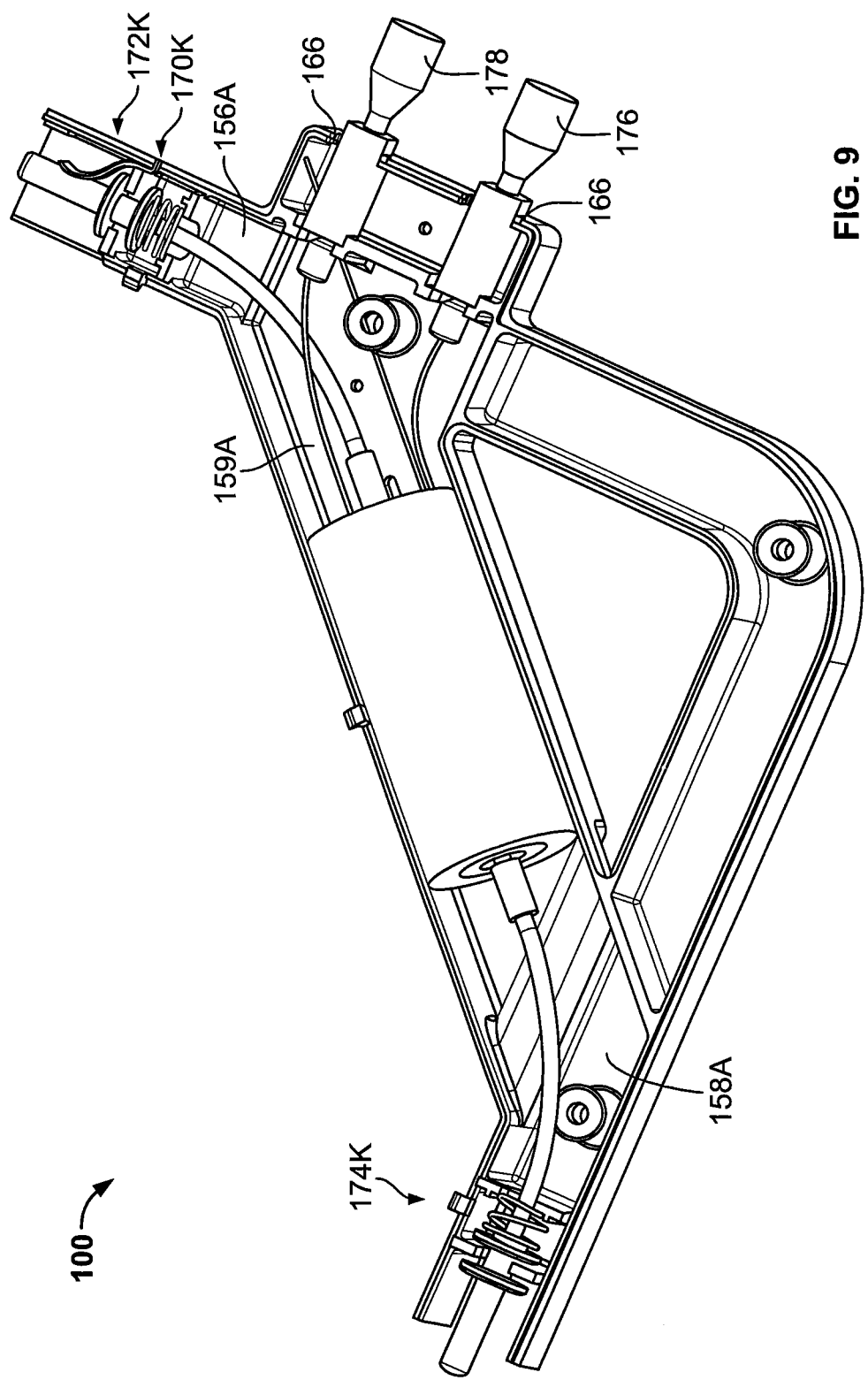
FIG. 9 is a fragmentary, top, front perspective view of the flow cell module.
Figure 10:
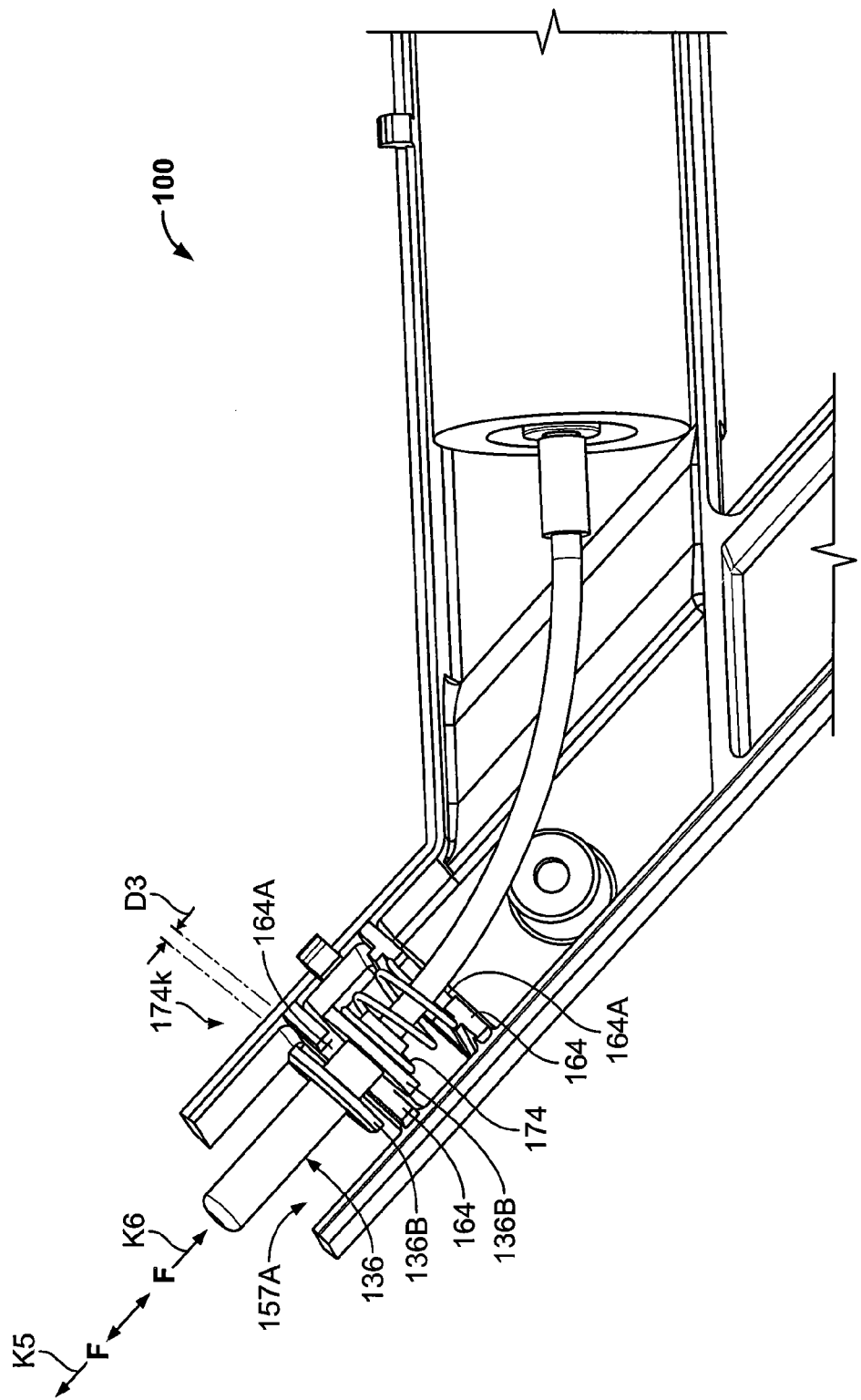
FIG. 10 is an enlarged, fragmentary, top, front perspective view of the flow cell module.
Figure 11:
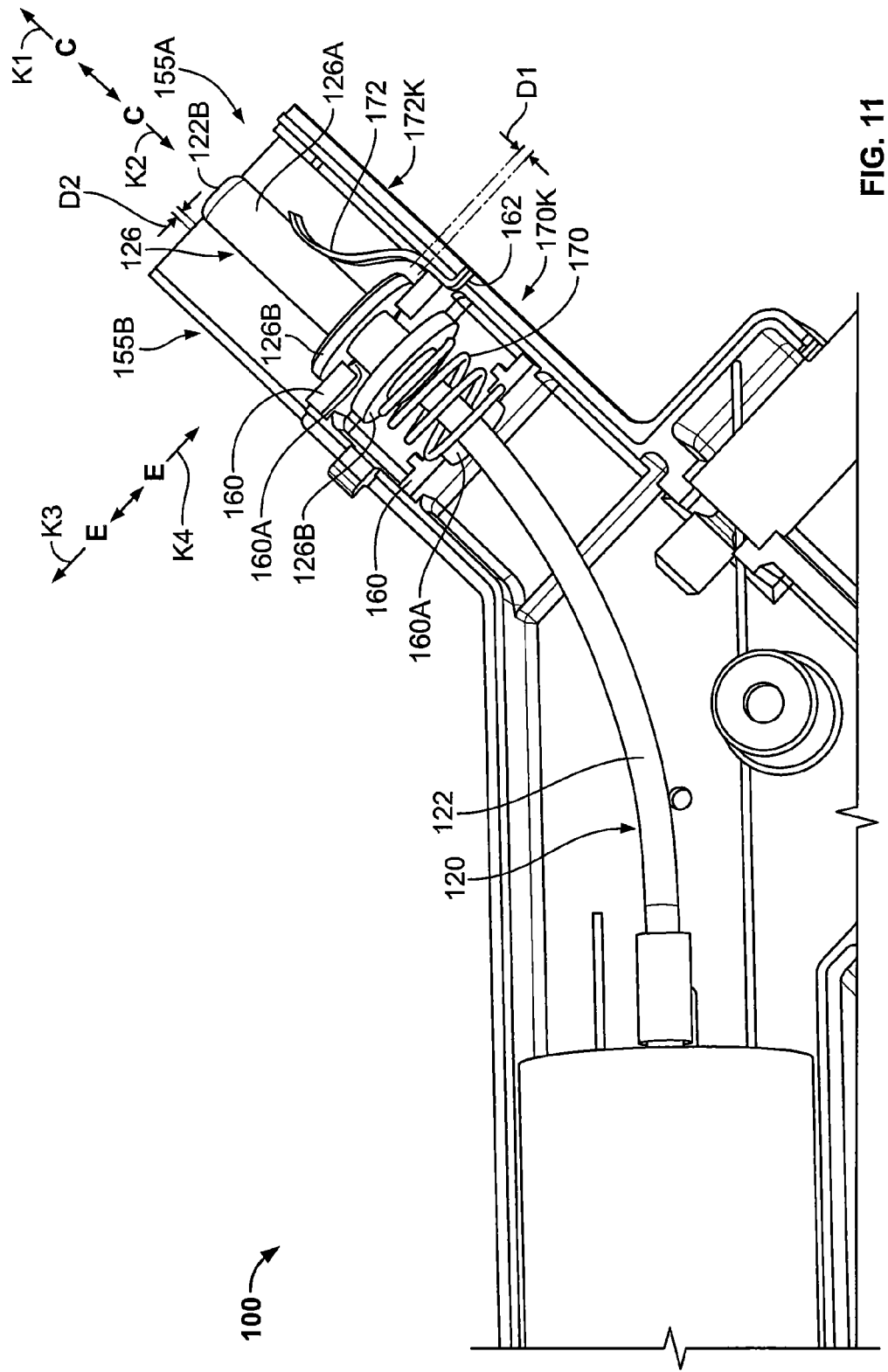
FIG. 11 is a further enlarged, fragmentary, top, front perspective view of the flow cell module.

The light source 20 (FIGS. 6 and 7) can be any suitable source of radiation or light for spectroscopic analysis. The light source 20 includes a housing 22 and an alignment device, structure or block 28. A lamp 24 is contained in the housing 22. According to some embodiments, the lamp 24 is a deuterium lamp. The alignment block 28 includes a V-shaped groove 28A defining a lengthwise axis A-A, and a lateral or sideward opening 28B. An opening or window 22A is provided in the housing 22. Light from the lamp 24 is emitted out of the housing 22 through the window 22A, which may include a lens. The window 22A can be aligned with the groove 28A.

Figure 4:
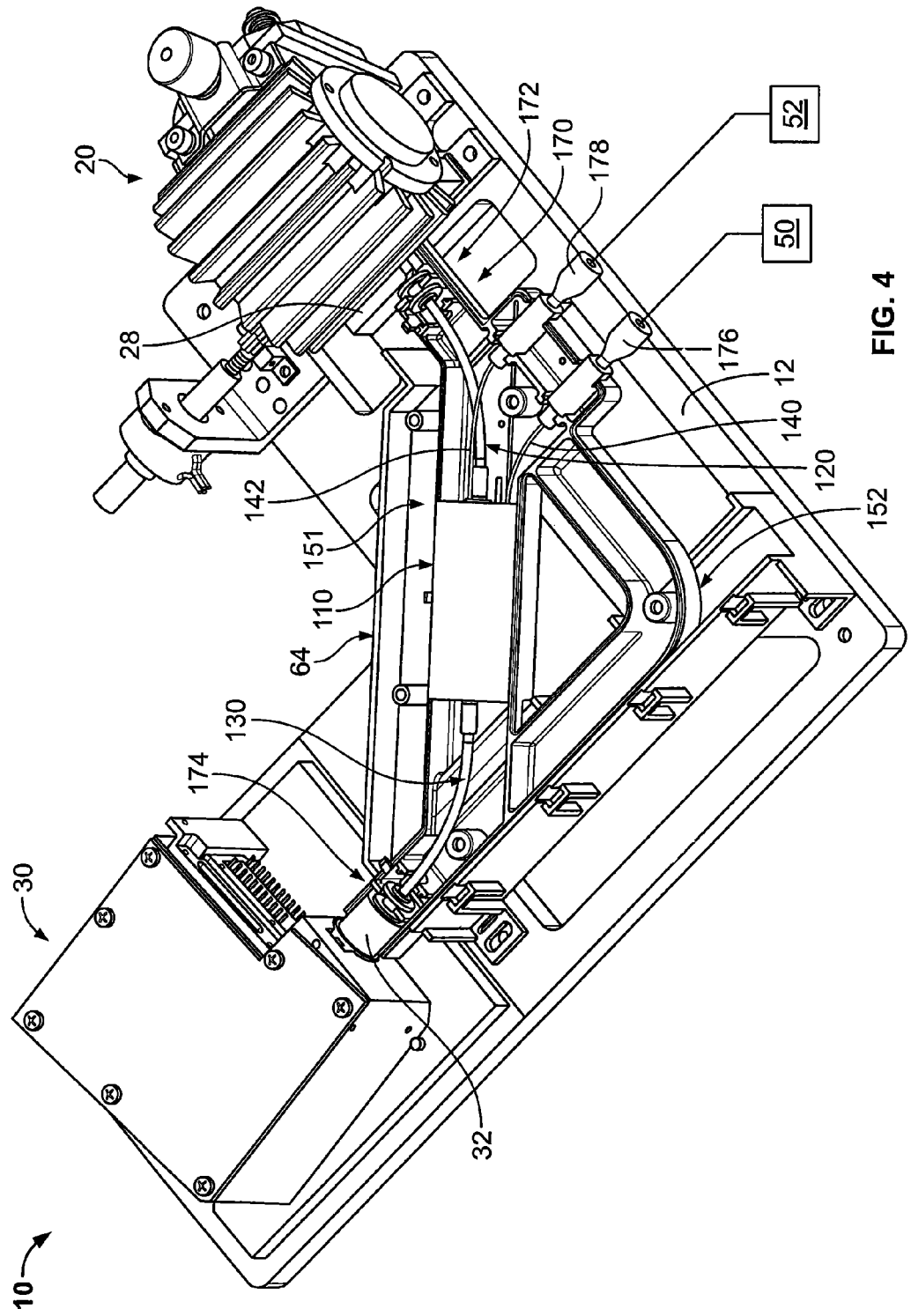
FIG. 4 is a fragmentary, perspective view of the subassembly of FIG. 3.
Figure 5:
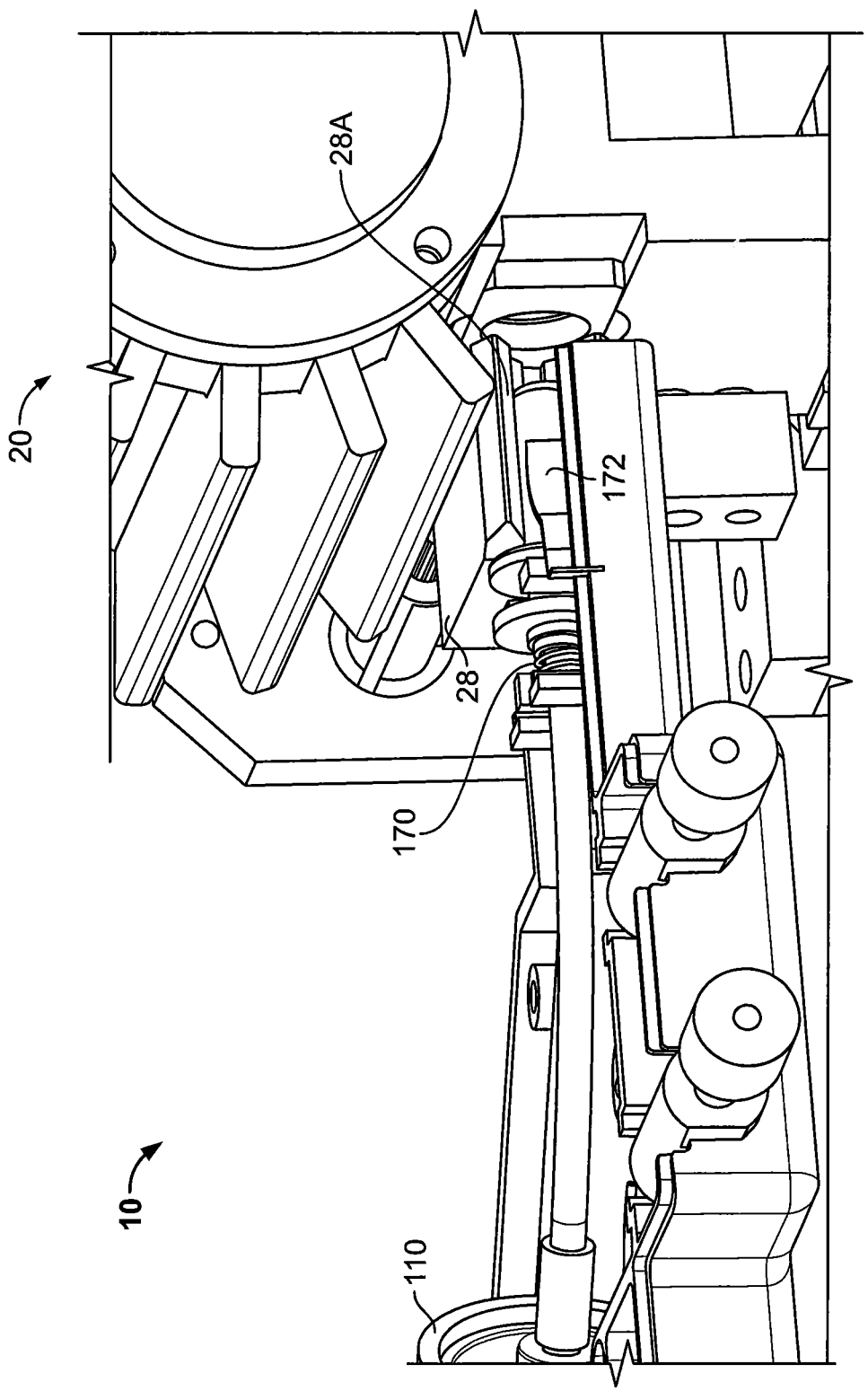
FIG. 5 is a further fragmentary, perspective view of the subassembly of FIG. 3.

The sensing device 30 (FIG. 4) may be any suitable sensing device or detector for spectroscopic analysis. According to some embodiments, the detector 30 is a spectrometer including a photodiode array (PDA). The detector 30 includes a fiber optic connector 32 for input of optical energy or signals for further processing.

The liquid sample source 50 may be any suitable source including a supply of the sample to be analyzed in a liquid solvent. According to some embodiments, the solvent is aqueous. The liquid sample receiver 52 may be a waste receptacle or a down line process. According to some embodiments, at least one of the liquid sample source 50 and the liquid sample receiver 52 is provided with a pump to generate a forced flow of the liquid sample through the flow cell module 100.

Figure 2:
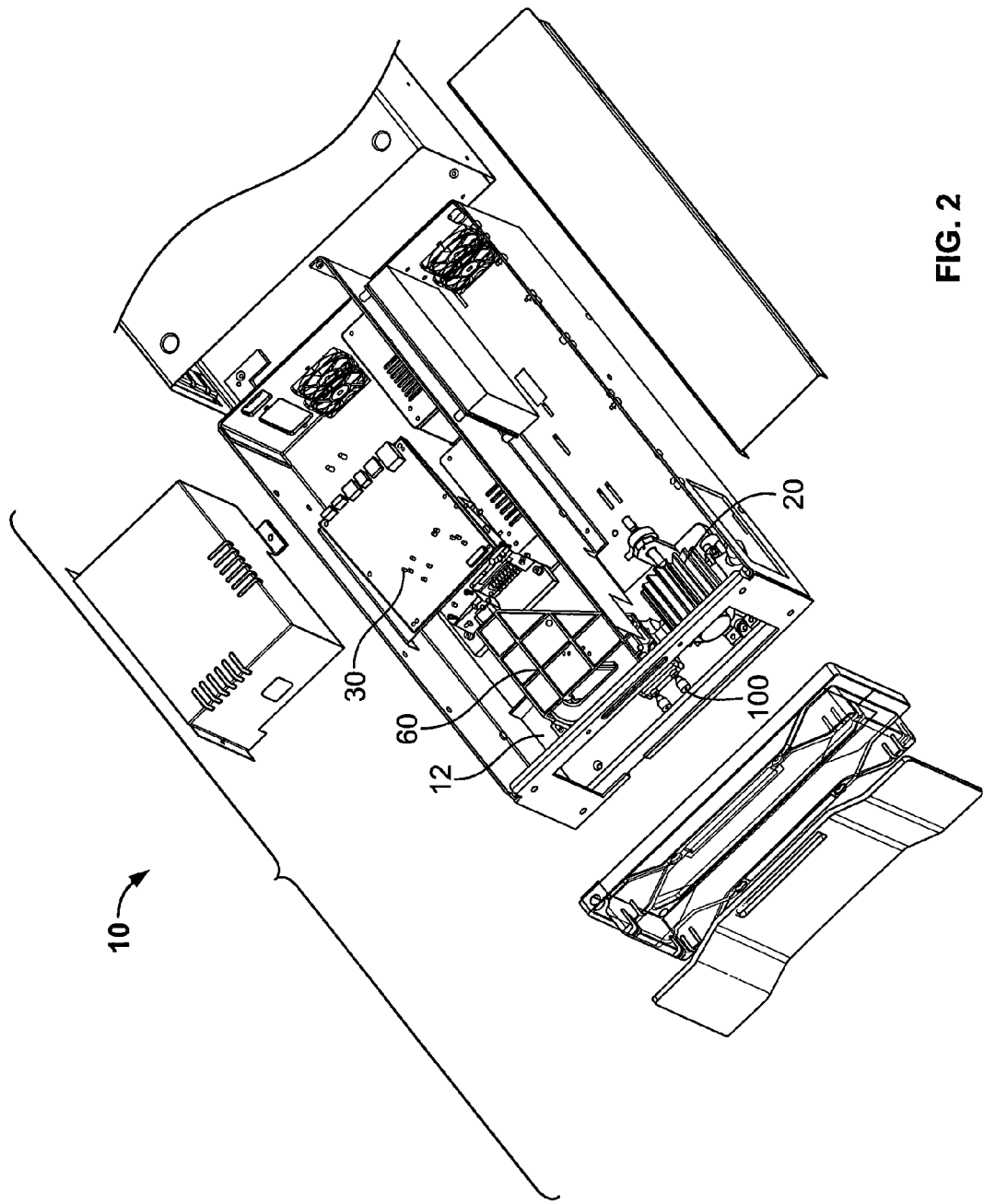
FIG. 2 is an exploded, front perspective view of the liquid sample analyzer of FIG. 1.

The carrier tray 60 (FIGS. 2 and 3) is secured to the base 12 and defines a holding cavity, socket or slot 64 and a front opening 62 communicating with the slot 64. The tray 60 has track rails 66 and a latch (not shown).

With reference to FIGS. 3-6 and 8-11, the flow cell module 100 includes a flow cell unit or assembly 110, a connectorized radiation input or source optical fiber 120, a connectorized radiation output or detector optical fiber 130, a liquid sample feed capillary tube 140, a liquid sample exit capillary tube 142, a module housing 150, an input connector axial biasing mechanism 170 (according to some embodiments and as shown, a coil spring), an input connector lateral biasing mechanism 172 (according to some embodiments and as shown, a leaf spring), an output connector biasing mechanism 174 (according to some embodiments and as shown, a coil spring), a liquid sample feed connector 176, and a liquid sample exit connector 178. The components 110, 120, 130, 140, 142, 170, 172, 174, 176, and 178 are mounted in the module housing 150, as discussed in more detail herein.

Figure 12:
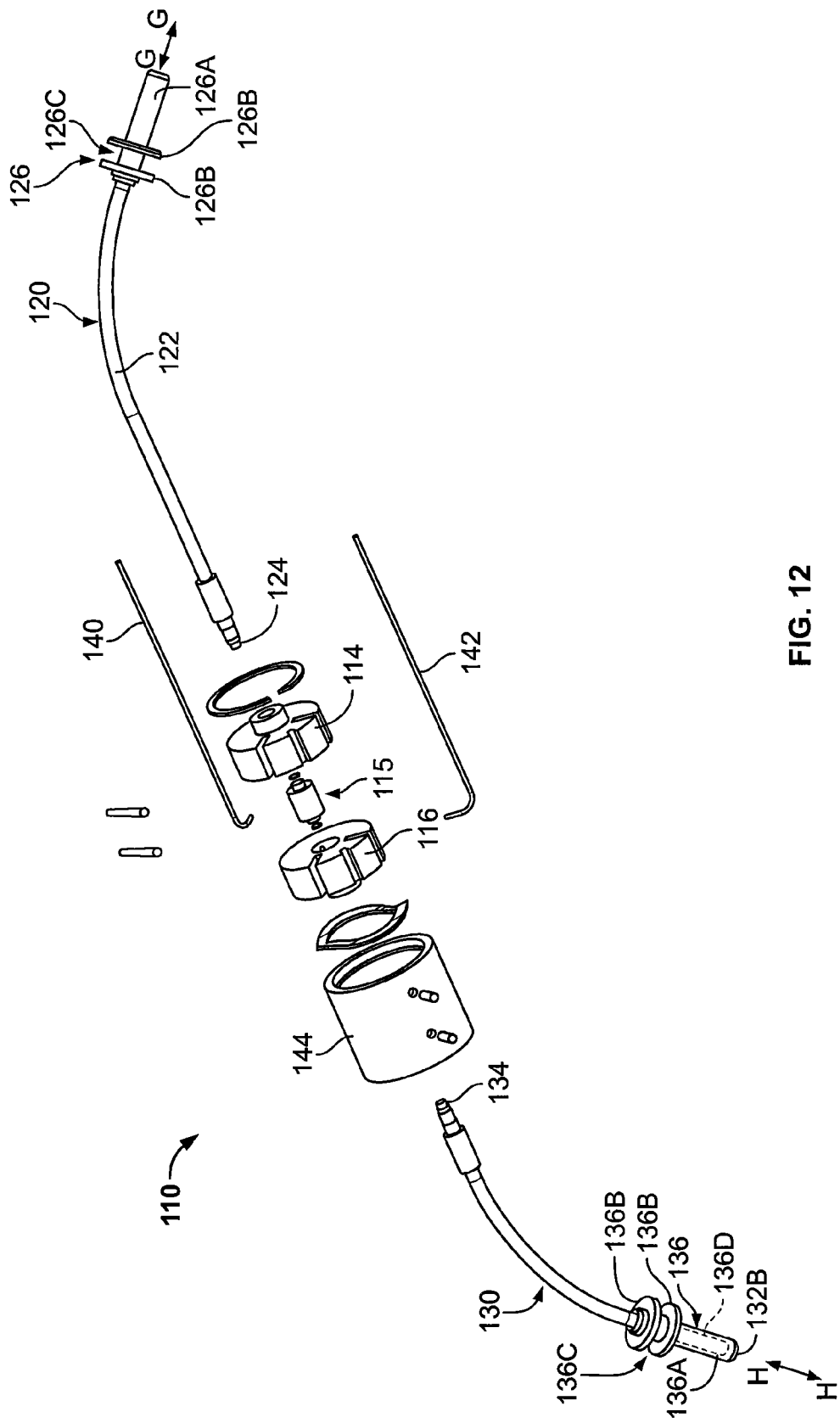
FIG. 12 is an exploded, perspective view of a flow cell assembly forming a part of the flow cell module.
Figure 13:
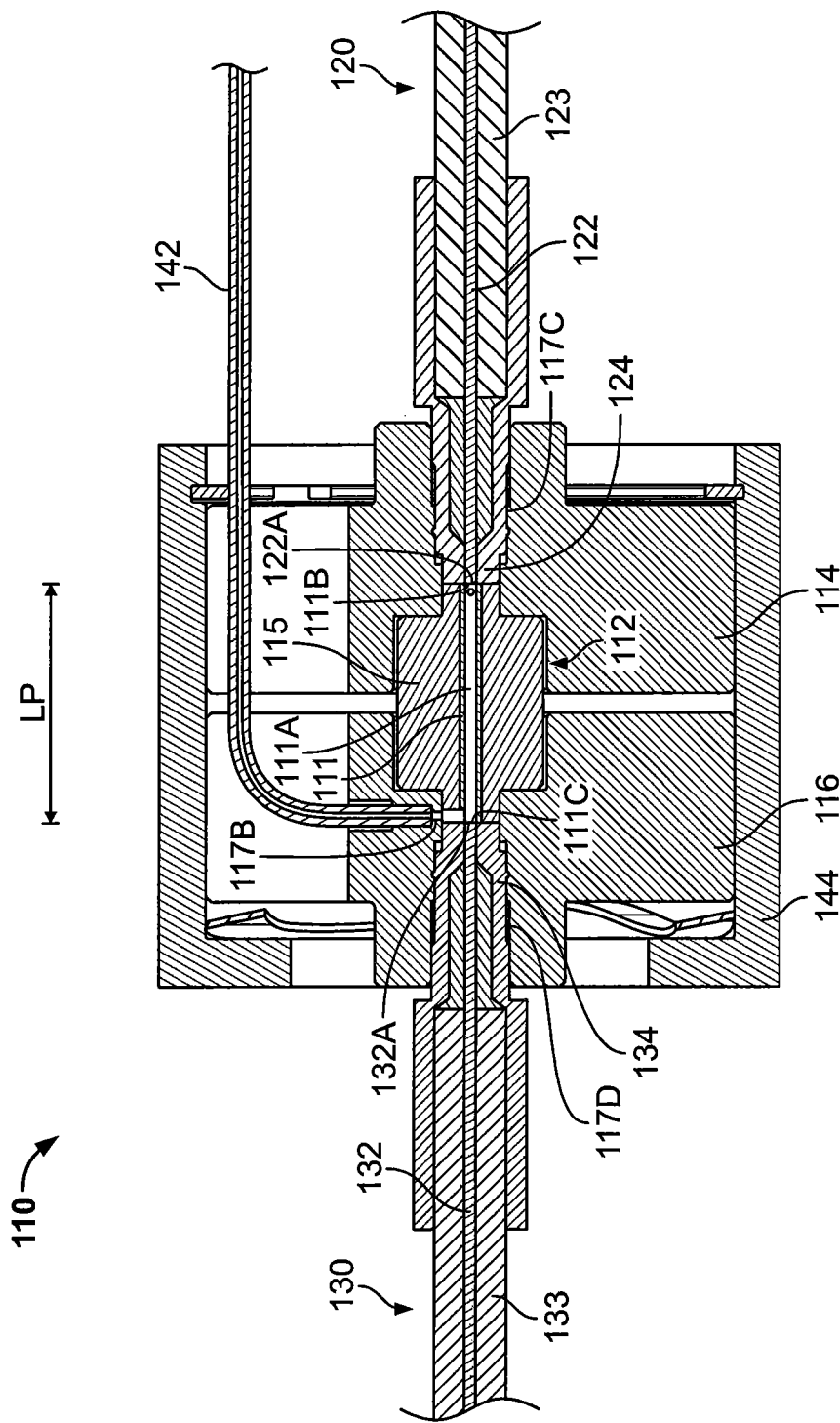
FIG. 13 is a cross-sectional view of the flow cell assembly.
Figure 14:
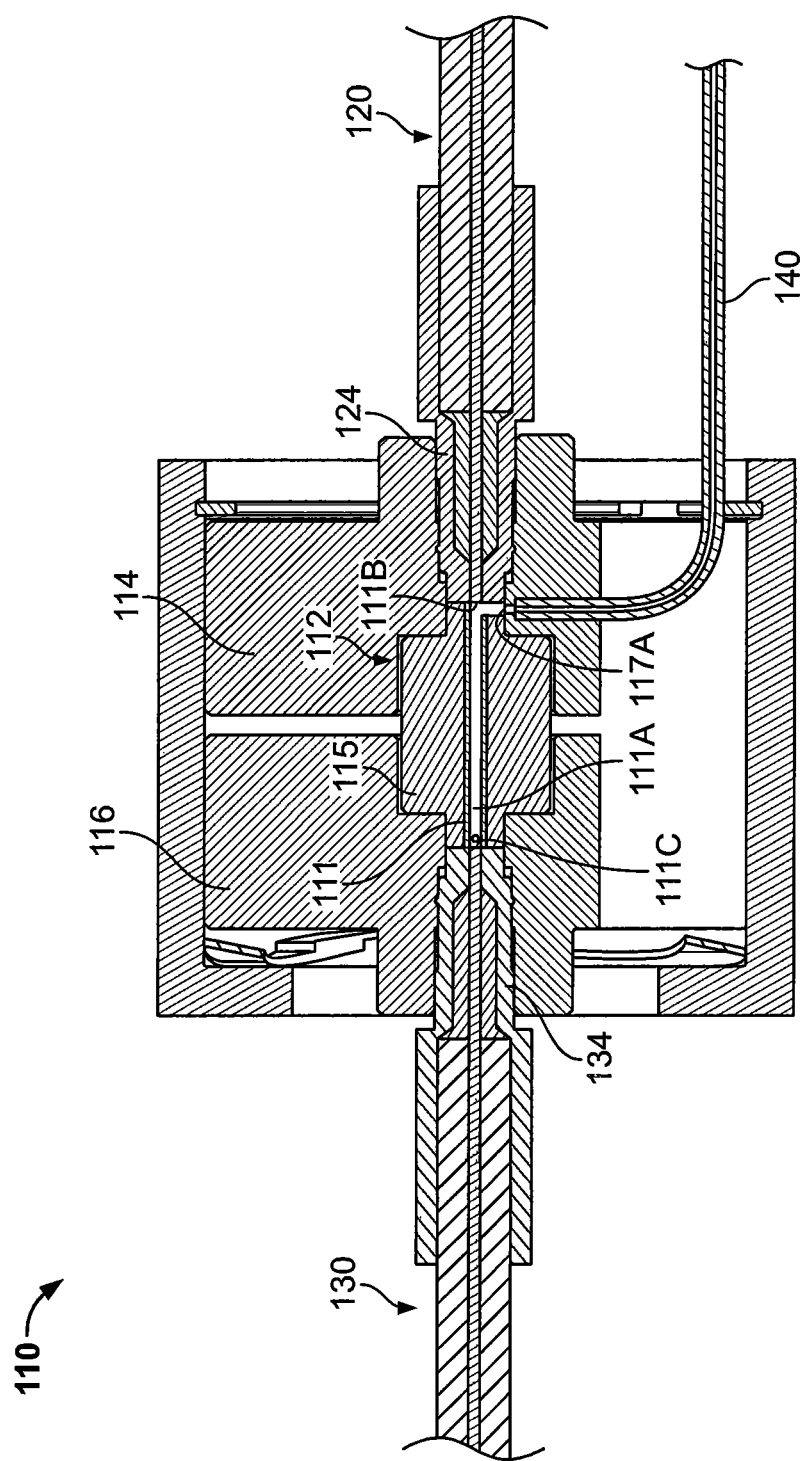
FIG. 14 is a further cross-sectional view of the flow cell assembly.

With reference to FIG. 12, the source connectorized fiber 120 includes a flexible optical fiber or waveguide 122, a ferrule 124, and a termination 126. The optical fiber 122 may be an optical fiber including a solid glass core and a solid glass cladding and may be covered in a protective jacket 123. The ferrule 124 is mounted on one end of the optical fiber 122 such that an output end face 122A is exposed adjacent and substantially flush with an end face of the ferrule 124. The termination 126 is mounted on the opposite end of the optical fiber 122 such that an input end face 122B of the optical fiber 122 is exposed. In use, the termination 126 is installed proximate the light source 20 such that light from the light source 20 is directed into the optical fiber 122 through the end face 122B and transmitted through the fiber 122 and out of the fiber 122 through the end face 122A.

The termination 126 includes a ferrule or shaft 126A and a pair of axially spaced apart flanges 126B extending radially outwardly from the shaft 126A and defining a slot 126C therebetween. A bore 126D (FIG. 6) extends through the shaft 126A and the fiber 122 extends through the bore 126D so that the fiber end face 122B is located at or proximate the terminal end of the termination 126. The termination 126 has a lengthwise axis G-G (FIG. 12) intersecting the end face 122B.

With reference to FIG. 12, the detector connectorized fiber 130 includes a flexible optical fiber 132 (which may be covered in a protective jacket 133), a ferrule 134, and a termination 136. The ferrule 134 is mounted on an end of the optical fiber 132 such that an input end face 132A is exposed adjacent and substantially flush with an input end face of the ferrule 134. The termination 136 is mounted on the opposite end of the fiber 132 such that an output end face 132B of the fiber 132 is exposed. In use, the termination 136 is mated with the fiber optic connector 32 of the detector 30 to transmit light from the end face 132A to the detector 30.

The termination 136 includes a ferrule or shaft 136A and a pair of axially spaced apart flanges 136B extending radially outwardly from the shaft 136A and defining a slot 136C therebetween. A bore 136D extends through the shaft 136A and the fiber 132 extends through the bore 136D so that the fiber end face 132B is located at or proximate the terminal end of the termination 136. The termination 136 has a lengthwise axis H-H (FIG. 12) intersecting the end face 132A.

The capillary tubes 140, 142 fluidly couple the flow cell assembly 110 to the liquid sample source 50 and the liquid sample receiver 52, respectively, via the connectors 176, 178. According to some embodiments, the capillary tubes 140, 142 are flexible. In some embodiments, the tubes 140, 142 are formed of fused silica or quartz. The tubes 140, 142 are terminated at the fluid connectors 176, 178 to which the liquid sample source 50 and the liquid sample receiver 52 are fluidly coupled.

In some embodiments, the flow cell assembly 110 includes a flow cell or liquid core waveguide 112 mounted in or between an entrance "T" member or joint member 114 and an exit "T" member or joint member 116, which are in turn mounted in a housing 118. The waveguide 112 may include a waveguide body 115 and a cladding layer 111 extending through the waveguide body 115.

The cladding layer 111 is tubular and continuous and its outer surface is in intimate contact with the inner surface of the waveguide body 115. In some embodiments, the layer 111 is bonded to or forms a tight interference fit with the inner surface of the waveguide body 115. The inner surface of the cladding layer 111 defines a passage or bore 111A extending axially fully through the waveguide body 115 and terminating at opposed end openings 111B, 111C.

The waveguide body 115 and the cladding layer 111 may be formed of any suitable materials. According to some embodiments, the waveguide body 115 is formed of a polymeric material. In some embodiments, the waveguide body 115 is formed of polyetheretherketone (PEEK). The cladding layer 111 maybe formed of a material having a lower refractive index than that of the liquid sample. According to some embodiments, the cladding layer 111 is formed of a fluoropolymer and, in some embodiments, an amorphous fluoropolymer. According to some embodiments, the cladding layer 11 is formed of an amorphous copolymer of perfluora-2,2-dimethyl-1,3-dioxole and tetrafluoroethylene, an example of which is sold by E.I. du Pont de Nemours (commonly referred to as DuPont) under the trademark Teflon AF 2400™. According to some embodiments, the cladding layer 111 has a thickness in the range of from about 0.005 to 0.010 inch and, in some embodiments, from about 0.010 to 0.020 inch. According to some embodiments, the cladding layer 111 is substantially free of any internal microbends or kinks.

The flow cell assembly 110 includes a fluid feed port 117A fluidly connecting the feed tube 140 to the end opening 111B of the waveguide bore 111A and a fluid exit port 117B fluidly connecting the exit tube 142 to the end opening 111C of the waveguide bore 111A. The flow cell 110 also includes a source fiber receiving bore 117C that receives the ferrule 126 and positions the fiber output end face 122A adjacent the end opening 111B, and a detector fiber receiving bore 117D that receives the ferrule 134 and positions the fiber end face 132A adjacent the end opening 111C.

The flow cell module housing 150 includes two subhousings 152, 154 collectively defining a chamber 151, an input leg 156, an output leg 158, and a flow cell holding leg 159. The input leg 156 terminates at an input end 155. The output leg 158 terminates at an output end 157. Axially facing end connection openings 155A and 157A are defined in the ends 155 and 157, respectively. Additionally, a laterally or sidewardly facing side connection opening 155B is defined in the input end 155 and intersects the opening 155A. The subhousings 152, 154 may be configured in the same or similar manner and therefore only the subhousing 152 will be described in detail below, it being understood that the subhousing 154 may likewise include the features discussed.

An input channel 156A is defined in the input leg 156, an output channel 158A is defined in the output leg 158, and a flow cell holding channel 159A is defined in the flow cell holding leg 159. A pair of integral, axially spaced apart spring retainer walls 160 are located adjacent the input end 155 and have slots 160A defined therein. A pair of integral, axially spaced apart spring retainer walls 164 are located adjacent the output end 157 and have slots 164A defined therein. A further spring retainer slot 162 is defined in a sidewall of the subhousing 152 adjacent the input end 155. Openings 166 are provided in the subhousing 152 to receive and retain the liquid sample connectors 176, 178. A guide slot 168 is defined in the body of the subhousing 152 to slideably receive a track rail 66 of the carrier tray 60.

The subhousings 152, 154 may be formed of any suitable material or materials. According to some embodiments, the subhousings 152, 154 are molded from a polymer. In some embodiments, the subhousings 152, 154 are formed of a solvent resistant material. In some embodiments, the subhousings 152, 154 are formed of PBT (Valox).

The flow cell assembly 110 is seated and contained in the chamber 151 in the flow cell holding leg 159, the connectorized source fiber 120 extends from the flow cell assembly 110 to the input end 155 through the legs 159 and 156, and the connectorized detector fiber 130 extends from the flow cell assembly 110 to the output end 157 through the legs 159 and 158. Notably, the flexibility of the connectorized fibers 120, 130 can permit a relatively compact configuration. The liquid sample tubes 140, 142 extend from the flow cell assembly 110 through the leg 159 and are terminated at the connectors 176, 178. Further conduits (e.g. flexible tubing) can be used to connect the connectors 176, 178 to the liquid sample source 50 and the liquid sample receiver 52. The connectors 176, 178 may be standard PEEK fittings for use in HPLC and may be finger tightened.

The connectorized fiber 120 is mounted in the slots 160A such that the outer spring retainer wall 160 (i.e., the wall 160 near the end 155) is axially captured between the flanges 126B of the termination 126. The coil spring 170 is mounted on the connectorized fiber 120 behind the inner flange 126B and is axially captured between the spring retainer walls 160. In this manner, a kinematic connection mechanism 170K or plunger mechanism is formed that biases the termination 126 toward the end opening 155A (in a direction K1 along an axis C-C) while also permitting the termination 126 to be displaced a limited stroke distance Dl along the axis C-C in an opposing direction K2. According to some embodiments, the axis C-C is substantially parallel to the terminal axis G-G.

Additionally, the leaf spring 172 is seated in the spring retainer slot 162 such that a leg 172A of the spring 172 bears against the shaft 126A of the termination 126, tending to push the shaft 126A along a lateral or sideward axis E-E toward the side opening 155B. In this manner, a kinematic connection mechanism 172K is formed that biases the shaft 126A inwardly along an axis E-E in a direction K3 while also permitting the termination 126 to be displaced a limited deflection distance D2 generally along the axis E-E in an opposing direction K4. The axis E-E is transverse to (and, in some embodiments and as shown, perpendicular to) the axis C-C.

The connectorized fiber 130 is mounted in the slots 164A such that the outer spring retainer wall 164 (i.e., the wall 164 near the end 157) is axially captured between the flanges 136B of the termination 136. The coil spring 174 is mounted on the connectorized fiber 130 behind the inner flange 136B and is axially captured between the spring retainer walls 164. In this manner, a kinematic connection mechanism 174K or plunger mechanism is formed that biases the termination 136 along an axis F-F in a direction K5 toward the opening 157A while also permitting the termination 136 to be displaced a limited stroke distance D3 along an axis F-F in an opposing direction K6. According to some embodiments, the axis F-F is substantially parallel to the termination axis H-H.

Once assembled, the flow cell module 100 can be installed in the liquid sample analyzer 10 as follows. The guide slots 168A of the flow cell module 100 are aligned with the track rails 66 of the carrier tray 60. The flow cell module 100 is pushed in an installation direction P until the terminations 126 and 136 operatively engage and seat in or on the fiber optic connector 32 of the detector 30 and the V-shaped groove 28A of the radiation source 20.

At the detector end 157, the fiber optic connector 32 is received through the end opening 157A to engage the fiber optic connector 136. The kinematic connection mechanism 170K permits some axial displacement of the termination 136 to accommodate variations in the installed position or to permit some deflection while transitioning to the installed position, while also biasing the termination 136 toward the connector 132 to provide a good connection.

At the source end 155, the alignment block 28 is received through the side opening 155B so that the termination shaft 126A is seated in the base or bottom of the V-shaped groove 28A with the fiber end face 132A facing and aligned with the window 22A in the source housing 22. In this manner, the fiber end face 132A is properly positioned to receive radiation from the lamp 24 emitted through the window 22A. The kinematic connection mechanism 172K permits some lateral displacement of the shaft 126A to accommodate variations in the installation path while ultimately biasing the shaft 126A into the bottom of the V-shaped groove 28A, which centers the shaft 126A. The kinematic connection mechanism 174K permits some axial displacement of the termination 126 to accommodate variations or misalignments during installation of the flow cell module 100.

In use, a flow of the liquid sample is pumped or otherwise driven from the liquid sample source 50, through the feed connector 176, through the feed tube 140, through the waveguide 112 (more particularly through the waveguide bore 111A from the end opening 111B to the end opening 111C), through the exit tube 142, and through the exit connector 178 to the liquid sample receiver 52.

Simultaneously, a beam of optical energy emitted from the lamp 24 of the source 20 is reflected off a mirror surface 29 and then transmitted, in sequence, through the window 22A, into the input fiber 122 through the end face 122A, through the fiber 122, into the waveguide bore 111A through the fiber end face 122B, through the liquid sample in the bore 111A, into the exit fiber 132 through the end face 132A, and through the fiber 132 to the input of the detector 30 through the fiber end face 132B. The liquid sample in the bore 111A serves as an optical core and the cladding layer 111 serves as an optical cladding providing total internal reflection. The waveguide 112 has an illuminated path length LP (i.e., the axial length of the column of liquid sample illuminated in the bore 111A) extending from the fiber end face 122A to the fiber end face 132A.

In an exemplary embodiment, the detector 30 is a PDA spectrometer including a photodiode array and a grating to divide an incident light beam into prescribed wave lengths (or ranges of wave lengths) and project the different wave lengths onto different respective photodiodes of the PDA. The liquid sample is axially illuminated by the source beam from the source 20. The illuminated liquid sample will absorb and thereby attenuate the light at different wave lengths in accordance with its composition. The voltage of each photodiode will be reduced in proportion to the reduction of its corresponding wave length in the light beam exiting the liquid sample through the optical fiber 132.

Liquid sample analyzers and flow cell assemblies according to embodiments of the technology can provide a number of benefits and advantages. Sensing devices such as PDA spectrometers typically require low flow cell dispersion and fast data rates and high light flux. It is desirable to provide a flow cell assembly that is compact and that can be flexibly integrated into a PDA spectrometer system.

The cladding sleeve 111, particularly when formed of a material as discussed hereinabove and providing total internal reflection, allows for a smaller volume flow cell without loss of optical signal, thereby increasing output resolution.

The flow cell module 100 is adaptable to multiple path lengths. The illuminated path length LP can be varied by simply providing a waveguide 112 having a different length and an outer housing 118 having a corresponding different length. According to some embodiments, flow cell assemblies as disclosed herein are provided having a path length in the range of from about 0.1 cm (e.g., 0.1 µl) to about 10 cm (e.g., 10 µl).

Liquid sample analyzers and flow cell modules of the present technology can facilitate flow cell insertion and removal. An operator can simply push (e.g., by hand) the flow cell module 100 to slide into the slot 64 until the connectors 132 and 136 fully mate. To remove, the operator can pull (e.g., by hand) the flow cell module 100 to slide the flow cell module 100 out of the slot 64. The latch (not shown) can prevent or inhibit unintended movement of the flow cell module 100 during operation.

The flow cell module 100 can be easily handled and installed by the operator without requiring optical alignment focusing. Rather, the kinematic mounting of the spring loaded fiber mounted termination 126 can ensure that the termination 126 is automatically and positively properly aligned with the source window 22A when the flow cell module 100 is fully inserted.

Advantageously, the flexible, compliant, kinematic mounting of the optical fiber terminations (e.g., by the kinematic connection mechanisms 170K, 172K, 174K) in accordance with embodiments of the invention can facilitate or assist in ensuring proper alignment between the optical fiber terminations and associated components (e.g., between the optical fiber end face 126B and the window 22A, and between the fiber optic end face 132B and fiber optic connector 32 of the detector 30). In this manner, the kinematic mounting arrangement (s) can compensate for tolerances between the components of the system.

The fluid connections between the flow cell module 100 and the liquid sample source 50 and the liquid sample receiver 52 can be easily made (e.g., by hand) using the integral connectors 176, 178, providing ease in changing fluid connections.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A flow cell module for use in a liquid sample analyzer, the liquid sample analyzer including a radiation source, a sensing device and a liquid sample source, the flow cell module comprising:
   a module housing;
   a liquid core waveguide mounted in the module housing and configured to receive a flow of a liquid sample from the liquid sample source;
   an output optical fiber disposed in the module housing and configured to transmit radiation from the liquid core waveguide to the sensing device;

an output termination on an output end of the output optical fiber, wherein the output termination is kinematically mounted in the module housing; and a kinematic connection mechanism operative to bias the output termination in a prescribed direction along a displacement axis while permitting displacement of the output termination in an opposing direction along the displacement axis;

wherein the kinematic connection mechanism includes a spring biasing the output termination in the prescribed direction.

2. The flow cell module of claim 1 wherein the output optical fiber is flexible.

3. The flow cell module of claim 1 wherein the kinematic connection mechanism is operative to bias the output termination relative to the module housing in the prescribed direction along the displacement axis while permitting displacement of the output termination in the opposing direction along the displacement axis.

4. The flow cell module of claim 3 wherein the kinematic connection mechanism is operative to push the output termination relative to the module housing in the prescribed direction.

5. The flow cell module of claim 3 wherein the kinematic connection mechanism is operative to bias the output termination relative to the module housing in the prescribed direction along the displacement axis while permitting displacement of the output termination with a limited deflection distance in the opposing direction along the displacement axis.

6. The flow cell module of claim 1 wherein the spring is a coil spring.

7. The flow cell module of claim 1 wherein the output termination includes a ferrule.

8. The flow cell module of claim 1 further including:
an input optical fiber disposed in the module housing and configured to transmit radiation from the radiation source to the liquid core waveguide; and
an input termination on an input end of the input optical fiber, wherein the input termination is kinematically mounted in the module housing.

9. A liquid sample analyzer having a holding slot and comprising:
a radiation source;
a sensing device;
a liquid sample source;
a flow cell module configured to be mounted in the holding slot and including:
a module housing;
a liquid core waveguide mounted in the module housing and configured to receive a flow of a liquid sample from the liquid sample source;
an output optical fiber disposed in the module housing and configured to transmit radiation from the liquid core waveguide to the sensing device; and
an output termination on an output end of the output optical fiber;
wherein the output termination is kinematically mounted in the module housing to facilitate alignment between the output termination and the sensing device when the flow cell module is inserted into the holding slot; and
wherein the flow cell module includes a kinematic connection mechanism that permits displacement of the output termination to accommodate variations in an installed position of the output termination and/or to permit deflection of the output termination while transitioning to the installed position.

10. The liquid sample analyzer of claim 9 wherein:
the sensing device includes a fiber optic connector; and
when the flow cell module is mounted in the holding slot, the output termination engages the fiber optic connector.

11. The liquid sample analyzer of claim 10 wherein the output termination includes a ferrule.

12. The liquid sample analyzer of claim 10 wherein the flow cell module further includes:
an input optical fiber disposed in the module housing and configured to transmit radiation from the radiation source to the liquid core waveguide; and
an input termination on an input end of the input optical fiber, wherein the input termination is kinematically mounted in the module housing;
wherein, when the flow cell module is mounted in the holding slot, the input optical fiber transmits radiation from the radiation source to the liquid core waveguide.

13. The flow cell module of claim 9 wherein the output optical fiber is flexible.

14. The flow cell module of claim 13 wherein the kinematic connection mechanism is operative to bias the output termination relative to the module housing in a prescribed direction along a displacement axis while permitting displacement of the output termination in an opposing direction along the displacement axis.

15. The flow cell module of claim 14 wherein the kinematic connection mechanism includes a spring biasing the output termination in the prescribed direction.

16. A flow cell module for use in a liquid sample analyzer, the liquid sample analyzer including a radiation source, a sensing device and a liquid sample source, the flow cell module comprising:
a module housing;
a liquid core waveguide mounted in the module housing and configured to receive a flow of a liquid sample from the liquid sample source;
an output optical fiber disposed in the module housing and configured to transmit radiation from the liquid core waveguide to the sensing device;
an output termination on an output end of the output optical fiber, wherein the output termination is kinematically mounted in the module housing; and
a kinematic connection mechanism operative to bias the output termination in a prescribed direction along a displacement axis while permitting displacement of the output termination in an opposing direction along the displacement axis;
wherein the kinematic connection mechanism is operative to bias the output termination relative to the module housing in the prescribed direction along the displacement axis while permitting displacement of the output termination with a limited deflection distance in the opposing direction along the displacement axis.

17. The flow cell module of claim 16 wherein the output optical fiber is flexible.

18. The flow cell module of claim 16 wherein the kinematic connection mechanism is operative to push the output termination relative to the module housing in the prescribed direction.

19. The flow cell module of claim 16 wherein the output termination includes a ferrule.

20. The flow cell module of claim 16 further including:
an input optical fiber disposed in the module housing and configured to transmit radiation from the radiation source to the liquid core waveguide; and an input termination on an input end of the input optical fiber, wherein the input termination is kinematically mounted in the module housing.

* * * * *

UNITED STATES PATENT AND TRADEMARK OFFICE
CERTIFICATE OF CORRECTION

PATENT NO. : 9,228,934 B2
APPLICATION NO. : 14/742066
DATED : January 5, 2016
INVENTOR(S) : Hanlon et al.

It is certified that error appears in the above-identified patent and that said Letters Patent is hereby corrected as shown below:

On Title Page:
Item (73), Assignee: Please correct "PerkinsElmer"
to read -- PerkinElmer --

Item (56), References Cited, Other Publications, Line 1:
Please correct "Stoma®"
to read -- Starna® --

Signed and Sealed this
Fifth Day of July, 2016

Michelle K. Lee
*Director of the United States Patent and Trademark Office*